(12) United States Patent
Thomas et al.

(10) Patent No.: US 7,652,032 B2
(45) Date of Patent: Jan. 26, 2010

(54) 5-THIOXYLOPYRANOSE COMPOUNDS

(75) Inventors: Didier Thomas, Saint-apollinaire (FR); Michel Bondoux, Fontaine-les-dijon (FR); Véronique Barberousse, Hauteville les Dijon (FR); Vincent Peyrou, Hauteville les Dijon (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 0 days.

(21) Appl. No.: 12/352,382

(22) Filed: Jan. 12, 2009

(65) Prior Publication Data

US 2009/0118325 A1 May 7, 2009

Related U.S. Application Data

(63) Continuation of application No. PCT/FR2007/051647, filed on Jul. 12, 2007.

(51) Int. Cl.
*A61K 31/4355* (2006.01)
*C07D 498/04* (2006.01)

(52) U.S. Cl. ...................... 514/301; 546/114
(58) Field of Classification Search ................. 514/301; 546/114
See application file for complete search history.

(56) References Cited

U.S. PATENT DOCUMENTS

| 4,432,973 A | 2/1984 | Picart |
| 4,877,808 A | 10/1989 | Samreth et al. |
| 5,101,048 A | 3/1992 | Bajgrowicz et al. |
| 5,169,838 A | 12/1992 | Samreth et al. |
| 7,470,671 B2 | 12/2008 | Barberousse et al. |

FOREIGN PATENT DOCUMENTS

| EP | 0 051 023 B1 | 5/1982 |
| EP | 0 365 397 A2 | 4/1990 |
| EP | 0 421 829 A1 | 4/1991 |
| EP | 0 421 829 B1 | 4/1991 |
| FR | 2 860 234 A1 | 4/2005 |
| WO | WO 2005/030785 A2 | 4/2005 |

OTHER PUBLICATIONS

International Search Report dated Nov. 2, 2007 including English translation of the relevant portion (Four (4) pages).

*Primary Examiner*—Taofiq A Solola
(74) *Attorney, Agent, or Firm*—Crowell & Moring LLP

(57) ABSTRACT

5-thioxylose compounds, especially 5-thioxylopyranose compounds, a process for their preparation, and their use for treating and/or inhibiting thromboses, especially venous thromboses. The compounds correspond to formula I:

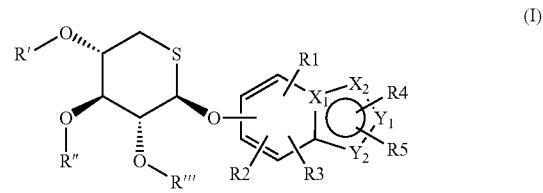

(I)

in which the pentapyranosyl group represents a free or substituted 5-thio-β-D-xylopyranosyl group; R', R" and R'" each independently represent a hydrogen atom, a $C_2$-$C_6$ acyl group, or two adjacent ones of them form a 1-methylethylidene bridge; $X_1$ and $X_2$ each represent carbon or nitrogen; $Y_1$ and $Y_2$ each independently represent carbon, nitrogen, sulfur or oxygen, with the proviso that if $Y_2$ represents oxygen or sulfur, then $Y_1$ represents carbon or nitrogen; $R_1$, $R_2$, $R_3$, $R_4$ and $R_5$ each independently represent hydrogen, a $COOR_6$ group where $R_6$ represents hydrogen or a $C_1$-$C_4$ alkyl group optionally substituted by a phenyl ring, a halogen atom or a —$COOR_6$ group; a $C_1$-$C_4$ alkoxy group; a $C_1$-$C_6$ acyl group; a benzoyl group or a phenyl ring; and the addition salts and/or active metabolites of such compounds.

10 Claims, No Drawings

5-THIOXYLOPYRANOSE COMPOUNDS

CROSS REFERENCE TO RELATED APPLICATIONS

This application is a continuation of international patent application no. PCT/FR2007/051647, filed Jul. 12, 2007, designating the United States of America and published in French on Jan. 17, 2008 as WO 2008/007027, the entire disclosure of which is incorporated herein by reference. Priority is claimed based on French patent application no. FR 0652954, filed Jul. 13, 2006.

BACKGROUND OF THE INVENTION

The present invention relates to new 5-thioxylose compounds, preferably 5-thioxylopyranose type derivatives, and also to the process for the preparation thereof and to the use thereof as an active ingredient of medicaments, in particular for use in the treatment or prevention of thromboses.

PRIOR ART

D-xylose derivatives are already known, for example through documents EP 051 023 B1, U.S. Pat. No. 4,877,808, EP 421 829 B1 and WO 05/030 785 or through the publication J. Med. Chem. Vol. 36 n° 7, p 898-903. These known compounds are recommended for reducing the risks of venous thrombosis in humans. The mechanism of action of these compounds appears to be an effect on plasma glycosaminoglycans (J. Biol. Chem., Vol 270 n° 6 p 2662-68, Thromb. Haemost. 1999, 81 p 945-950).

SUBJECT OF THE INVENTION

A new family of compounds, derived from thioxylose, which have good antithrombotic activity and which can be synthesized efficiently, has now been discovered.

DESCRIPTION

The new compounds according to the invention are characterized in that they are chosen from:
a) the compounds of formula:

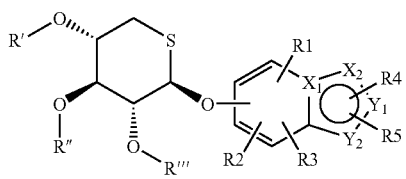

(I)

in which:
the pentapyranosyl group represents a free or substituted 5-thio-β-D-xylopyranosyl group,
R', R" and R''' each independently represent a hydrogen atom or a $C_2$-$C_6$ acyl group, or two of them, adjacent, form a 1-methylethylidene bridge,
$X_1$ and $X_2$ each represent a carbon or nitrogen atom,
$Y_1$ and $Y_2$ each represent, independently of one another, a carbon, nitrogen, sulfur or oxygen atom, on condition that, if $Y_2$ represents an oxygen or sulfur atom, $Y_1$ represents a carbon or nitrogen atom, $R_1$, $R_2$, $R_3$, $R_4$ and $R_5$ represent, independently of one another, a hydrogen atom, a —$COOR_6$ group where $R_6$ represents a hydrogen atom or a $C_1$-$C_4$ alkyl, a $C_1$-$C_4$ alkyl group optionally substituted with a phenyl ring, a halogen atom or a —$COOR_6$ group, a $C_1$-$C_4$ alkoxy group, a $C_2$-$C_6$ acyl group, a benzoyl group or a phenyl ring;
b) the addition salts of the compounds of formula I;
c) the active metabolites of the compounds of formula I.

The invention also relates to the compounds of formula I for the use thereof as a pharmacologically active substance.

In particular, the invention relates to the use of at least one substance chosen from the compounds of formula I and the nontoxic addition salts thereof, for the preparation of a medicament, for use in human or animal therapy, for the prevention or treatment of thromboses, in particular venous thromboses. Since the compounds according to the invention are active according to a method of action involving glycosaminoglycans, they may be of use as an active ingredient of a medicament for use in the treatment or prevention of any other diseases in which glycosaminoglycans are involved.

DETAILED DESCRIPTION

In formula I, the term "$C_1$-$C_4$ alkyl group" is intended to mean a saturated hydrocarbon-based chain containing from 1 to 4 carbon atoms, which is linear or branched, or partially or completely cyclized, the cyclized portion containing 3 or 4 carbon atoms. Examples of $C_1$-$C_4$ alkyl groups are in particular methyl, ethyl, propyl, butyl, 1-methylethyl, 1,1-dimethylethyl, 1-methylpropyl, 2-methylpropyl, cyclopropyl or cyclopropylmethyl groups.

The term "$C_2$-$C_6$ acyl group" is intended to mean an R—CO— group, in which R represents an alkyl group as defined above containing from 1 to 5 carbon atoms. Examples of $C_2$-$C_6$ acetyl groups are in particular acetyl, propanoyl, butanoyl, pentanoyl or hexanoyl groups, and also homologues thereof in which the chain may be branched.

The term "$C_1$-$C_4$ alkoxy group" is intended to mean an RO— group, in which R is an alkyl group containing from 1 to 4 carbon atoms as defined above. By way of examples of $C_1$-$C_4$ alkoxy groups, mention may be made of methoxy, ethoxy, propoxy, butoxy, 1-methylethoxy, 1,1-dimethylethoxy, 1-methylpropoxy, 2-methylpropoxy or cyclopropylmethoxy groups.

The term "addition salts" is intended to mean the addition salts obtained by reacting a compound of formula I with a mineral or organic acid. Preferably, they are pharmaceutically acceptable addition salts. The hydrates or solvates of the compounds of formula I or of the salts of the compounds of formula I are also an integral part of the invention.

Among the mineral acids that are suitable for salifying a basic compound of formula I, hydrochloric acid, hydrobromic acid, phosphoric acid and sulfuric acid are preferred. Among the organic acids that are suitable for salifying a basic compound of formula I, methanesulfonic acid, benzenesulfonic acid, toluenesulfonic acid, maleic acid, fumaric acid, oxalic acid, citric acid, tartaric acid, lactic acid and trifluoroacetic acid are preferred.

The term "active metabolites" is intended to mean the compounds produced in the biological environment from the compounds of formula I and which have a pharmacological activity of the same nature as the compounds of formula I, described in the present application. By way of example, the compounds of formula I in which $R_1$ represents an acyl group can be metabolized by reduction of the ketone function to an alcohol function (—CHOH—) so as to give a new compound (metabolite) which conserves a pharmacological activity of the same nature as that of the compounds of formula I.

Compounds which illustrate the invention are those of formula I in which:

the pentapyranosyl group represents a free or acylated, preferably acetylated, 5-thio-β-D-xylopyranosyl group; or $X_1$ and $Y_2$ represent a nitrogen atom and $X_2$ and $Y_1$ represent a carbon atom; or $Y_2$ represents an oxygen atom and $X_1$, $X_2$ and $Y_1$ represent a carbon atom; or $Y_2$ represents a nitrogen atom and $X_1$, $X_2$ and $Y_1$ represent a carbon atom; or $X_2$ represents an oxygen atom, $Y_2$ represents a nitrogen atom and $X_1$ and $Y_1$ represent a carbon atom; or $X_2$ represents a sulfur atom, $Y_2$ represents a nitrogen atom and $X_1$ and $Y_1$ represent a carbon atom; or $X_2$ and $Y_2$ represent a nitrogen atom and $X_1$ and $Y_1$ represent a carbon atom; or $Y_1$ represents a nitrogen atom and $Y_2$ represents an oxygen atom and $X_1$ and $X_2$ represent a carbon atom; or $Y_1$ represents an oxygen atom and $Y_2$ represents a nitrogen atom and $X_1$ and $X_2$ represent a carbon atom; or $X_2$, $Y_1$ and $Y_2$ represent a nitrogen atom and $X_1$ represents a carbon atom; or $X_1$, $X_2$ and $Y_2$ represent a nitrogen atom and $Y_1$ represents a carbon atom.

Among the compounds according to the present invention, preference is given to those in which $X_1$ and $Y_2$ represent a nitrogen atom and $X_2$ and $Y_1$ represent a carbon atom, and also the compounds in which $X_1$, $X_2$ and $Y_2$ represent a nitrogen atom and $Y_1$ represents a carbon atom.

Among the compounds according to the invention, preference is also given to the compounds in which R is a hydrogen atom or the —$COCH_3$ group.

The compounds of formula I according to the invention may be prepared by carrying out the glycosylation methods known to those skilled in the art, in particular:

a) the method of HELFERICH described in the book "The Carbohydrate, Chemistry and Biochemistry", 2nd edition, Academic Press, New York-London 1972, Volume IA pages 292-294, by condensation of a peracetylated sugar with an aromatic hydroxyheterocycle in the presence of a Lewis acid;

b) the method of KOENIGS-KNORR (idem, pages 295-299) by condensation of a halogenated acylose with a hydroxyl group of phenolic nature, in the presence of a proton acceptor, such as mercuric cyanide, silver imidazolate or silver trifluoromethylsulfonate;

c) the method of MITSONOBU (Duynstee et al., Tet. Lett. 39 (1998), p. 4129-4132) by condensation of a partially acetylated acylose and of an aromatic hydroxyheterocycle in the presence of an alkylazodicarboxylate and of a Lewis base.

The compounds of formula I are preferably prepared according to methods derived from the processes referenced above.

According to a first general process, the following steps are carried out, consisting in:

a) reacting an aromatic system comprising a hydroxyl group that is phenolic in nature, of formula:

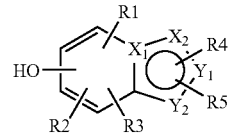

II in which:

$X_1$ and $X_2$ each represent a carbon or nitrogen atom, $Y_1$ and $Y_2$ represent a carbon, nitrogen, sulfur or oxygen atom, with the condition that, if $Y_2$ represents an oxygen or sulfur atom, $Y_1$ represents a carbon or nitrogen atom, $R_1$, $R_2$, $R_3$, $R_4$ and $R_5$ represent, independently of one another, a hydrogen atom, a —$COOR_6$ group where $R_6$ represents a hydrogen atom or a $C_1$-$C_4$ alkyl, a $C_1$-$C_4$ alkyl group optionally substituted with a phenyl ring, a halogen atom or a —$COOR_6$ group, a $C_1$-$C_4$ alkoxy group, a $C_2$-$C_6$ acyl group, a benzoyl group or a phenyl ring, with a 5-thioxylopyranose derivative of formula:

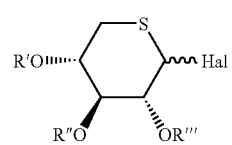

(III-D)

in which Hal represents a halogen, preferably bromine, and R', R" and R''' represent a $C_2$-$C_6$ acyl group, preferably the acetyl group, in an aprotic solvent such as acetonitrile or toluene, in the presence of a silver salt, in particular silver oxide or silver imidazolate, or of a zinc salt (in particular the oxide or the chloride) in an anhydrous medium, at a temperature of between 25 and 110° C. for 1 to 10 hours, so as to obtain the compound of formula:

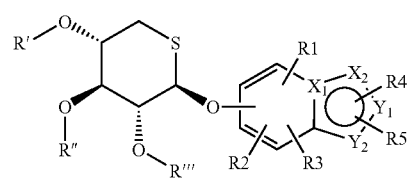

I in which $X_1$, $X_2$, $Y_1$, $Y_2$, R', R", R''', $R_1$, $R_2$, $R_3$, $R_4$ and $R_5$ keep the same meaning as in the starting compounds;

b) if necessary, reacting the compound of formula I obtained above with a solution of ammonia in methanol so as to perform the deacylation of the thioxylopyranosyl residue and replace the acyl groups with hydrogen atoms and to obtain the compound of formula:

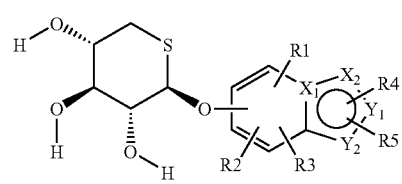

Ia in which $X_1$, $X_2$, $Y_1$, $Y_2$, $R_1$, $R_2$, $R_3$, $R_4$ and $R_5$ keep the same meaning as above;

c) if necessary, reacting one of the compounds I or Ia obtained above with an acid according to methods known to those skilled in the art, so as to obtain the corresponding addition salt.

As a variant of step b) described above, the replacing of the acyl group with a hydrogen atom may be carried out by the action of a metal alkoxide, preferably sodium methoxide, in a catalytic amount, in methanol, at a temperature of between 0 and 30° C. and for 0.5 to 2 hours, so as to obtain the compound of formula Ia from the compound of formula I in which R represents a $C_2$-$C_6$ acyl group.

According to a second process, the compounds of formula I can be obtained by the action of tetra-O-acetyl-5-thioxylopyranose of formula:

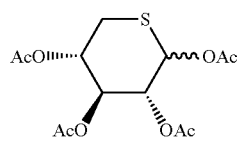

(IV-D)

in which Ac represents the acetyl group, with a compound of formula:

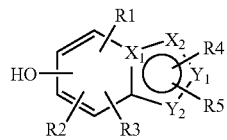

II in which:

X$_1$ and X$_2$ each represent a carbon or nitrogen atom,

Y$_1$ and Y$_2$ represent a carbon, nitrogen, sulfur or oxygen atom, with the condition that, if Y$_2$ represents an oxygen or sulfur atom, Y$_1$ represents a carbon or nitrogen atom, R$_1$, R$_2$, R$_3$, R$_4$ and R$_5$ represent, independently of one another, a hydrogen atom, a —COOR$_6$ group where R$_6$ represents a hydrogen atom or a C$_1$-C$_4$ alkyl, a C$_1$-C$_4$ alkyl group optionally substituted with a phenyl ring, a halogen atom or a —COOR$_6$ group, a C$_1$-C$_4$ alkoxy group, a C$_2$-C$_6$ acyl group, a benzoyl group or a phenyl ring, in an aprotic solvent, such as, for example, dichloromethane, in the presence of a catalyst of Lewis acid type, for example tin tetrachloride, at a temperature of between 20 and 60° C. and for 1 to 2 hours, so as to obtain the compound of formula:

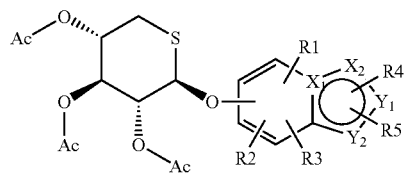

Ib in which X$_1$, X$_2$, Y$_1$, Y$_2$, R$_1$, R$_2$, R$_3$, R$_4$ and R$_5$ keep the same meaning as in the starting compounds.

The compound of formula Ib can subsequently be reacted, according to the protocol described in the above process, so as to obtain the unsubstituted pyranosyl compound of formula Ia and/or a salt with an acid.

The compounds of formula II mentioned above are products which may be commercially available or readily synthesized by those skilled in the art according to techniques described in the literature.

According to a third process, the compounds according to the invention may also be prepared by direct glycosylation, according to a process consisting in reacting a heteroaromatic derivative having a hydroxyl group of phenolic nature, with 2,3,4-tri-O-acetyl-5-thio-D-xylopyranose, in the presence of an alkylazodicarboxylate compound, such as diethylazodicarboxylate, of a Lewis base, such as triphenylphosphine, and of an aprotic polar solvent, such as tetrahydrofuran at a temperature of between −20° C. and 70° C., for 5 minutes to 72 hours, so as to obtain the corresponding glycosylated compound.

This compound may subsequently be reacted according to the protocol described in the above process, so as to obtain the unsubstituted pyranosyl compound of formula Ia and/or a salt with an acid.

The compounds according to the invention in which X$_1$ and Y$_2$ represent a nitrogen atom and X$_2$ and Y$_1$ represent a carbon atom (derivatives of the imidazo[1,2-α]pyridine family) of formula:

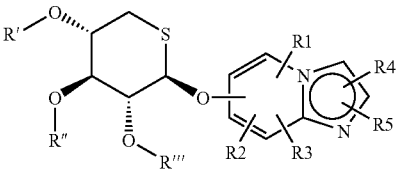

V may also be prepared by cyclization between a glycosylated pyridine having an amine group in the ortho-position with respect to the nitrogen of the pyridine ring and a carboxylated chlorinated derivative (J. J. Kaminski et al, J. Med. Chem, 28 (7), 1985 p 876).

According to this process, the following steps are carried out, consisting in:

a) reacting a compound of formula:

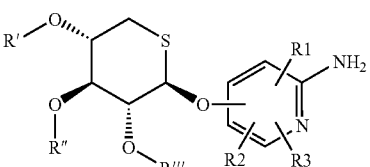

VI in which R', R'' and R''' represent a C$_2$-C$_6$ acyl group, and R$_1$, R$_2$ and R$_3$ independently represent a hydrogen atom, a C$_1$-C$_4$ alkyl group optionally substituted with a phenyl ring or a halogen atom, a C$_1$-C$_4$ alkoxy group, a C$_2$-C$_6$ acyl group, a benzoyl group or a phenyl ring, with an α-halogenated ketone of formula:

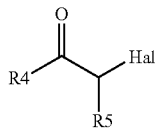
VII in which Hal represents a halogen atom, preferably chlorine or bromine, and $R_4$ and $R_5$ independently represent a hydrogen atom, a —$COOR_6$ group where $R_6$ represents a hydrogen atom or a $C_1$-$C_4$ alkyl, a $C_1$-$C_4$ alkyl group optionally substituted with a phenyl ring, a halogen atom or a $COOR_6$ group, a $C_1$-$C_4$ alkoxy group, a $C_2$-$C_6$ acyl group, a benzoyl group or a phenyl ring;

in the presence of a protic polar solvent, such as ethanol, at a temperature of between 60° C. and 130° C., for 5 minutes to 4 hours, so as to obtain the compound of formula:

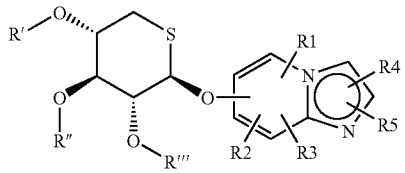
V in which R, $R_1$, $R_2$, $R_3$, $R_4$ and $R_5$ keep the same meaning as in the starting products, b) if necessary, carrying out a deprotection reaction to deprotect the 2,3,4-tri-O-acetyl-5-thio-β-D-xylopyranosyl group, so as to obtain the compound of formula V in which R', R" and R'" represent a hydrogen atom.

The compounds according to the invention in which $X_1$, $X_2$ and $Y_2$ represent a nitrogen atom and $Y_1$ represents a carbon atom (derivatives of the [1,2,4]triazolo[1,5-a]pyridine family), of formula:

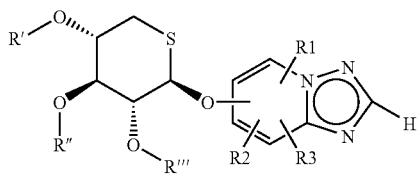
VIII may also be prepared by cyclization between a glycosylated N,N-dimethyl-N'-2-pyridinylmethanimidamide and hydroxylamine-O-sulfonic acid.

According to this process, the following steps are carried out, consisting in:

a) reacting a compound of formula:

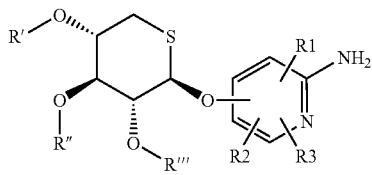
IX in which R', R" and R'" represent a $C_2$-$C_6$ acyl group, and $R_1$, $R_2$ and $R_3$ independently represent a hydrogen atom, a $C_1$-$C_4$ alkyl group optionally substituted with a phenyl ring or a halogen atom, a $C_1$-$C_4$ alkoxy group, a $C_2$-$C_6$ acyl group, a benzoyl group or a phenyl ring, with the dimethylformamide diacetal:

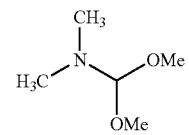
X in the presence of a protic polar solvent, such as ethanol, at a temperature of between 60° C. and 130° C., for 5 minutes to 4 hours, so as to obtain the compound of formula:

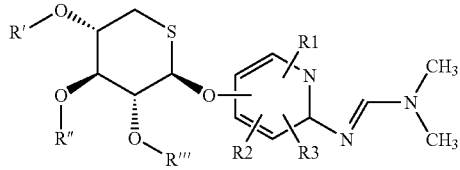
XI in which R', R", R'", $R_1$, $R_2$ and $R_3$ keep the same meaning as in the starting products, b) reacting this compound of formula XI with hydroxylamine-O-sulfonic acid, in a polar solvent such as, for example, methanol, in the presence of pyridine and at a temperature in the region of ambient temperature, for 1 to 3 hours, so as to obtain the [1,2,4]triazolo[1,5-a]pyridinyl 2,3,4-tri-O-acetyl-5-thio-β-D-xylopyranoside of formula VIII, c) if necessary, carrying out a deprotection reaction to deprotect the 2,3,4-tri-O-acetyl-5-thio-β-D-xylopyranosyl group, so as to obtain the compound of formula VIII in which R', R" and R'" represent a hydrogen atom.

According to the invention, certain compounds of formula I are such that R' and R" together represent a 1-methylethylidene bridge and R'" represents a hydrogen atom, or R" and R'" together represent a 1-methylethylidene bridge and R' represents a hydrogen atom. These compounds may be respectively represented by the following formulae:

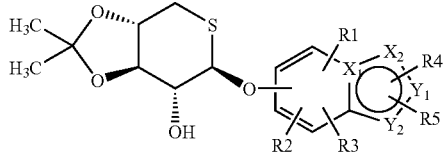

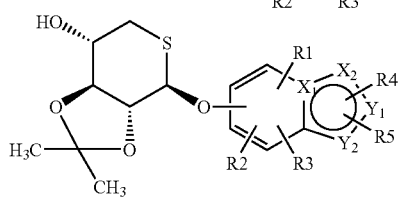

These compounds may be obtained starting from a compound of formula I in which R', R" and R'" represent a hydrogen atom, by reacting 2-methoxypropene, in an anhydrous polar solvent such as, for example, dimethylformamide, in the presence of an acid such as camphorsulfonic acid, at a temperature of between 15 and 70° C. and for 2 to 48 hours. The compounds are subsequently isolated and purified according to methods known to those skilled in the art, for example by crystallization or by chromatography.

In general, 2,3,4-tri-O-acetyl-5-thio-α-D-xylopyranosyl bromide or tetra-O-acetyl-5-thio-α-D-xylopyranose is preferably used when it is a question of obtaining a β-D-5-thioxylopyranose derivative.

The glycosylation reactions described above most commonly result in a mixture of the isomers of α and β configuration and it is generally necessary to optimize the operating conditions in order to obtain proportions favorable to the β-configuration isomer. For this same reason, it may also be necessary to perform purifications, either by recrystallization or by chromatography, so as to obtain the pure β-isomer.

The purpose of the following examples is to illustrate the invention, and they can in no way limit the scope thereof. In these examples, the melting points have been measured with a Kofler bench or a capillary tube and the nuclear magnetic resonance spectral values are characterized by the chemical shift calculated relative to TMS, by the number of protons associated with the signal and by the form of the signal (s for singlet, d for doublet, t for triplet, q for quadruplet, m for multiplet). The working frequency and the solvent used are indicated for each compound. Ambient temperature is 20° C.±4° C.

The following abbreviations have been used:
mM signifies millimol ($10^{-3}$ mol)
$CHCl_3$ denotes chloroform
$CH_3OH$ denotes methanol
DME denotes dimethoxyethane
DMF denotes dimethylformamide
DMSO denotes dimethyl sulfoxide
THF denotes tetrahydrofuran
TFA denotes trifluoroacetic acid.

PREPARATION 1

2-amino-3-pyridinyl 2,3,4-tri-O-acetyl-5-thio-β-D-xylopyranoside 1.45 g of palladium-on-charcoal at 10% is added to a solution of 14.5 g (35.4 mM) of 2-nitro-3-pyridinyl 2,3,4-tri-O-acetyl-5-thio-β-D-xylopyranoside in 290 ml of THF. The mixture is stirred under a hydrogen atmosphere at ambient temperature for 15 hours and then filtered. The filtrate is concentrated under reduced pressure. The expected product is obtained in the form of a beige solid with a yield of 98%.

Mp=145° C.
$[\alpha]_D^{23}$=−68° (c=0.44; DMSO).

PREPARATION 2

5-[(2,3,4-tri-O-acetyl-5-thio-D-xylopyranosyl)oxy]-1H-indole-1-carboxylic Acid 1,1-dimethylethyl Ester A solution of 1.75 g (7.51 mM) of 5-hydroxy-1H-indole-1-carboxylic acid tert-butyl ester in 25 ml of THF, 2.73 g (13.5 mM) of diisopropylazodicarboxylate and 3.54 g (13.5 mM) of triphenylphosphine are added to a solution of 2.85 g (9.75 mM) of 2,3,4-tri-O-acetyl-5-thio-D-xylopyranose in 50 ml of THF. The reaction mixture is stirred at 45° C. for 3 hours and then concentrated under reduced pressure. The evaporation residue is dissolved in ethyl acetate and the organic phase is washed with a 1N solution of sodium hydroxide, and then with a concentrated aqueous solution of ammonium chloride. The organic phase is subsequently dried over magnesium sulfate and concentrated under reduced pressure. The evaporation residue is purified by $C_{18}$-grafted silica chromatography, elution being carried out with an acetonitrile/water mixture (7/3; v/v). The desired product is obtained in the form of a pale yellow solid with a yield of 11%.

Mp=58-62° C.

PREPARATION 3

2-methyl-8-hydroxyimidazo[1,2-α]pyridine

A solution of 1.27 g (5.8 mM) of dimethylcarbamic acid 2-methylimidazo[1,2-α]pyridin-7-yl ester in 15 ml of methanol is added to a solution of sodium methoxide obtained from 0.2 g (8.7 mM) of sodium and 20 ml of methanol. The reaction mixture is brought to reflux for 15 hours and then cooled. The pH of the medium is then brought to 8.5 with a 2N solution of sulfuric acid, and then concentrated under reduced pressure. The evaporation residue is purified by silica gel chromatography, elution being carried out with a dichloromethane/methanol mixture (9/1; v/v). The expected product is obtained in the form of a brown solid with a yield of 87%.

Mp=154° C.

PREPARATION 4

2-methyl-6-methoxyimidazo[1,2-α]pyridine 0.74 g (8.04 mW of chloroacetone is added to a solution of 0.5 g (mM) of 2-amino-5-methoxypyridine in 17 ml of ethanol. The mixture is refluxed for 20 hours and then concentrated under reduced pressure. Ethyl acetate is added to the evaporation residue and the organic phase is washed with a saturated aqueous solution of sodium bicarbonate and then with a saturated solution of sodium chloride. The organic phase is subsequently dried over magnesium sulfate, filtered, and concentrated under reduced pressure. The evaporation residue is purified by $NH_2$ (amino group)-grafted silica gel chromatography, elution being carried out with a toluene/isopropyl alcohol mixture (99/1; v/v). The expected product is obtained in the form of an orange oil with a yield of 54%.

$^1H$ NMR (300 MHz; DMSO) δ=8.15 (d, 1H); 7.57 (s, 1H); 7.34 (d, 1H); 16.94 (dd, 1H); 3.77 (s, 3H); 2.29 (s, 3H).

PREPARATION 5

2-methyl-6-hydroxyimidazo[1,2-α]pyridine

A mixture composed of 1.92 g (11 mM) of 2-methyl-6-methoxyimidazo[1,2-α]pyridine and of 7.26 g (45 mM) of pyridinium hydrobromide is heated to melting point for 8 hours. The mixture is then cooled and water is added thereto. The aqueous phase is brought to a basic pH with sodium bicarbonate and extracted with ethyl acetate. The organic phase is washed with water, dried over magnesium sulfate, filtered, and concentrated under reduced pressure. The desired product is thus obtained in the form of a beige solid with a yield of 30%.

Mp=174° C.

PREPARATION 6

N,N-dimethyl-N'-[3-[(2,3,4-tri-O-acetyl-5-thio-β-D-xylopyranosyl)oxy]-2-pyridinyl]-methanimidamide 0.31 g (2.6 mM) of 1,1-dimethoxy-N,N-dimethylethanamine (N,N-dimethylformamide dimethylacetal) is added to a solution of 1 g (2.6 mM) of 2-amino-3-pyridinyl 2,3,4-tri-O-acetyl-5-thio-β-D-xylopyranoside (Preparation 1) in 10 ml of ethanol. The mixture is heated, in a microwave-compatible container, with stirring at 120° C. for 20 minutes in a microwave oven. The reaction mixture is subsequently concentrated under reduced pressure. The residue obtained is purified by silica gel chromatography, elution being carried out with ethyl acetate. The desired product is obtained in the form of a white solid with a yield of 46%.

Mp=120° C.

$[\alpha]_D^{32}=-82°$ (c=0.19; DMSO).

PREPARATION 7

2,1-benzisoxazol-7-ol 18.5 ml of a 1M solution of boron tribromide in dichloromethane are added to a solution of 1.38 g (9.25 mM) of 7-methoxy-2,1-benzisoxazole in 50 ml of dichloromethane cooled to −78° C., and the mixture is then stirred at ambient temperature overnight. The reaction medium is poured into water and the mixture is brought to pH=7-8 by adding a solution of sodium carbonate, and then extracted with dichloromethane. The organic phase is dried over magnesium sulfate and concentrated under vacuum. The crude product obtained is purified by silica gel chromatography, elution being carried out with a methylcyclohexane/ethyl acetate mixture (gradient of 100/0 to 50/50; v/v). The expected product is obtained in the form of a yellow solid with a yield of 10%.

$^1$H NMR (300 MHz; DMSO) δ=10.46 (s, 1H); 9.69 (s, 1H); 7.11 (d, 1H); 6.87 (dd, 1H); 6.54 (d, 1H).

PREPARATION 8

3-methyl-1,2-benzisoxazol-6-ol 1.98 g of 1-(2,4-dihydroxyphenyl)ethanone oxime (12 mM) and 1 g of potassium hydroxide (18 mM) are refluxed for 4 days in a methanol/water mixture (100 ml/100 ml). The reaction medium is subsequently concentrated under reduced pressure, acidified to pH=1 with 1N HCl, and then extracted with ethyl acetate. The organic phase obtained is dried over magnesium sulfate and concentrated under reduced pressure. The evaporation residue is purified by silica gel chromatography (methylcyclohexane/ethyl acetate gradient of 70/30 to 30/70; v/v). The expected product is obtained in the form of a white solid (0.39 g) with a yield of 22%.

Mp=122-136° C.

EXAMPLE 1

2-methylimidazo[1,2-α]pyridin-8-yl 2,3,4-tri-O-acetyl-5-thio-β-D-xylopyranoside

Process A 3.6 g (0.39 mM) of chloroacetone are added to a solution of 3 g (7.8 mM) of 2-amino-3-pyridinyl 2,3,4-tri-O-acetyl-5-thio-β-D-xylopyranoside obtained according to preparation 1, in 15 ml of ethanol. The mixture is heated, in a microwave-compatible container, with stirring at 120° C. for 30 minutes. The reaction mixture is subsequently concentrated under reduced pressure. The residue obtained is dissolved in ethyl acetate and the organic phase is washed successively with a saturated aqueous solution of sodium bicarbonate, with water and with a saturated solution of sodium chloride, and dried over magnesium sulfate. The organic phase is subsequently filtered and concentrated under reduced pressure. 3.8 g of crude product are obtained, which product is directly used without further purification for the following step (described in example 2).

Process B:

0.44 g (3 mM) of 8-hydroxy-2-methylimidazo[1,2-α]pyridine, 1.18 g (4.5 mM) of triphenylphosphine and 3.46 g (4.5 mM) of diethylazodicarboxylate supported on polystyrene resin (1.3 mM/g) are added to a solution of 1.32 g (4.5 mM) of 2,3,4-tri-O-acetyl-5-thio-β-D-xylopyranose in 30 ml of THF cooled to −10° C. The reaction mixture is stirred at −10° C. for 30 minutes, and then at ambient temperature for 15 hours. The reaction mixture is subsequently filtered and then concentrated under reduced pressure. The residue obtained is dissolved in ethyl acetate and the organic phase is washed with a 1N solution of sodium hydroxide, and then with water. The organic phase is subsequently dried over magnesium sulfate and concentrated under reduced pressure. The evaporation residue is purified by reverse-phase chromatography on $C_{18}$-grafted silica, elution being carried out with a water/acetonitrile gradient. The desired product is obtained in the form of a white solid with a yield of 14%.

Mp=180° C.

$[\alpha]_D^{28}=-80°$ (c=0.25; DMSO).

EXAMPLE 2

2-methylimidazo[1,2-α]pyridin-8-yl 5-thio-β-D-xylopyranoside

The product obtained according to example 1, in 40 ml of a 7 M solution of ammonia in methanol, is stirred at ambient temperature for 15 hours. The reaction mixture is concentrated under reduced pressure and the crude product obtained is purified by silica gel chromatography, elution being carried out with a dichloromethane/methanol mixture (gradient of 100/0 to 80/20; v/v). The product obtained is stirred into 200 ml of cold water and then filtered. The desired product is obtained in the form of a white powder with a yield of 53%.

Mp=145° C.

$[\alpha]_D^{30}=-89°$ (c=0.40; DMSO).

EXAMPLE 3

2-phenylimidazo[1,2-α]pyridin-8-yl 2,3,4-tri-O-acetyl-5-thio-β-D-xylopyranoside

By carrying out the process in a manner similar to process A of example 1, starting from 2-chloro-1-phenylethanone, the desired product is obtained in the form of an ecru solid with a yield of 52%.

Mp=205° C.

$[\alpha]_D^{29}=-94°$ (c=0.38; DMSO).

EXAMPLE 4

2-phenylimidazo[1,2-α]pyridin-8-yl 5-thio-β-D-xylopyranoside

By carrying out the process in a manner similar to example 2, starting from the product obtained in example 3, the desired product is obtained in the form of a white solid with a yield of 42%.

Mp=173° C.

$[\alpha]_D^{29}=-77°$ (c=0.48; DMSO).

EXAMPLE 5

3-methylimidazo[1,2-α]pyridin-8-yl 2,3,4-tri-O-acetyl-5-thio-β-D-xylopyranoside

By carrying out the process in a manner similar to process A of example 1, starting from 2-chloropropanal, the desired product is obtained in the form of a white solid with a yield of 24%.

Mp=150° C.
$[\alpha]_D^{29}$=−83° (c=0.25; DMSO).

EXAMPLE 6

3-methylimidazo[1,2-α]pyridin-8-yl 5-thio-β-D-xylopyranoside

By carrying out the process in a manner similar to example 2, starting from the product obtained in example 5, the desired product is obtained in the form of a white solid with a yield of 57%.

Mp=119° C.
$[\alpha]_D^{29}$=−69° (c=0.38; DMSO).

EXAMPLE 7

2-acetyl-7-benzofuranyl 2,3,4-tri-O-acetyl-5-thio-β-D-xylopyranoside

A mixture composed of 1.93 g (14.1 mM) of anhydrous zinc chloride, 1 g (5.7 mM) of 2-acetyl-7-hydroxybenzofuran and 2.2 g of molecular sieve 13× is stirred into 13 ml of toluene and 13 ml of acetonitrile. The mixture is brought to 90° C. and 1.42 g (14.1 mM) of triethylamine and 2.22 g (6.27 mM) of 2,3,4-tri-O-acetyl-5-thio-D-xylopyranosyl bromide are added, while maintaining the mixture at the temperature of 90° C. The mixture maintained at 90° C. is then stirred for 20 minutes. The mixture is subsequently cooled, 65 ml of a 0.5 N solution of sodium hydroxide are added, and the resulting mixture is stirred for one hour. The medium is filtered and the precipitate is washed with ethyl acetate. The filtrate is subsequently separated by settling out. The organic phase is washed with a saturated aqueous solution of ammonium chloride, dried over magnesium sulfate, and concentrated under reduced pressure. The evaporation residue is purified by silica gel chromatography, elution being carried out with a cyclohexane/ethyl acetate mixture (7/3; v/v). The desired product is obtained in the form of a yellowish solid with a yield of 37%.

Mp=208-209° C.
$[\alpha]_D^{27}$=−77° (c=0.48; DMSO).

EXAMPLE 8

2-acetyl-7-benzofuranyl 5-thio-β-D-xylopyranoside 0.118 ml of a solution of sodium methoxide at 18.7% by weight in methanol (0.41 mM) is added, at ambient temperature, to a suspension of 1.85 g (4.1 mM) of product obtained according to example 7, in 40 ml of methanol. The reaction mixture is stirred at 40° C. for 70 minutes. The medium is subsequently cooled while stirring, and then Amberlite IR 120H+ resin is added. The resin is subsequently removed by filtration and rinsed with a methanol/tetrahydrofuran mixture. The filtrate is concentrated under reduced pressure and the residue obtained is triturated in ether and filtered. After filtration, the solid obtained is dried. The expected compound is thus obtained in the form of yellow crystals with a yield of 76%.

Mp=116-120° C.
$[\alpha]_D^{24}$=−73° (c=0.55; DMSO).

EXAMPLE 9

1H-indol-5-yl 2,3,4-tri-O-acetyl-5-thio-β-D-xylopyranoside 0.089 g (0.82 mM) of anisole and 7 ml of trifluoroacetic acid are added to a solution of 0.42 g (0.82 mM) of product obtained according to preparation 2, in 60 ml of dichloromethane. The reaction mixture is stirred at reflux for 1 hour and 30 minutes and then, after cooling, is concentrated under reduced pressure. The evaporation residue is purified by silica gel chromatography, elution being carried out with a toluene/acetone mixture (95/5; v/v). The desired product is obtained in the form of a colorless oil with a yield of 30%.

EXAMPLE 10

1H-indol-5-yl 5-thio-β-D-xylopyranoside

By carrying out the process in a manner similar to example 8, starting from the product obtained in example 9, the desired product is obtained in the form of a white solid with a yield of 53%.

NMR (250 MHz, DMSO) δ=10.95 (s, 1H), 7.29 (m, 3H), 6.84 (dd, 1H), 6.35 (m, 1H), 5.45 (d, 1H), 5.04 (d, 1H), 4.99 (d, 1H J=8.88 Hz), 4.94 (d, 1H), 3.52 (m, 2H), 3.13 (m, 1H), 2.55 (m, 2H).

EXAMPLE 11

2-methyl-5-benzothiazolyl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 2-methyl-5-hydroxybenzothiazole, the desired product is obtained in the form of white crystals with a yield of 6%.

Mp 158° C. (recrystallized from isopropyl alcohol).
$[\alpha]_D^{27}$=−23° (c=0.48; $CH_3OH$).

EXAMPLE 12

2-methyl-5-benzothiazolyl 5-thio-β-D-xylopyranoside

By carrying out the process in a manner similar to example 8, starting from the product obtained in example 11, the desired product is obtained in the form of white crystals with a yield of 73%.

Mp=210-211° C.
$[\alpha]_D^{27}$=−79° (c=0.41; $CH_3OH$).

EXAMPLE 13

5-acetyl-4,7-dimethoxy-6-benzofuranyl 2,3,4-tri-O-acetyl-5-thio-β-D-xylopyranoside By carrying out the process in a manner similar to example 7, starting from 2,3,4-tri-O-acetyl-5-thio-D-xylopyranosyl bromide and 5-acetyl-4,7-dimethoxy-6-hydroxybenzofuran, the desired product is obtained and is directly used in the following deprotection step without prior purification.

EXAMPLE 14

5-acetyl-4,7-dimethoxy-6-benzofuranyl 5-thio-β-D-xylopyranoside

By carrying out the process in a manner similar to example 2, starting from the product obtained in example 13, the desired product is obtained in the form of a white solid with a yield of 25%.

Mp=207-209° C.
$[\alpha]_D^{26} = -40°$ (c=0.29; DMSO).

EXAMPLE 15

4-benzoxazolyl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 4-hydroxybenzoxazole, the desired product is obtained in the form of a white solid with a yield of 41%.

Mp=139° C.
$[\alpha]_D^{29} = -61°$ (c=0.23; DMSO).

EXAMPLE 16

4-benzoxazolyl 5-thio-β-D-xylopyranoside

By carrying out the process in a manner similar to example 2, starting from the product obtained in example 15, the desired product is obtained in the form of an off-white powder with a yield of 61%.

Mp=172° C.
$[\alpha]_D^{29} = 94°$ (c=0.19; DMSO).

EXAMPLE 17

7-benzofuranyl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 7-hydroxybenzofuran, the desired product is obtained in the form of a white solid with a yield of 14%.

Mp=152° C.
$[\alpha]_D^{30} = -47°$ (c=0.32; DMSO).

EXAMPLE 18

7-benzofuranyl 5-thio-β-D-xylopyranoside

By carrying out the process in a manner similar to example 2, starting from the product obtained in example 17, the desired product is obtained in the form of a white solid with a yield of 50%.

Mp=160° C.
$[\alpha]_D^{30} = -85°$ (c=0.24; DMSO).

EXAMPLE 19

3-benzoyl-5-benzofuranyl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 3-benzoyl-5-hydroxybenzofuran, the desired product is obtained in the form of a white solid with a yield of 20%.

Mp=182° C.
$[\alpha]_D^{27} = +1°$ (c=0.22; DMSO).

EXAMPLE 20

3-benzoyl-5-benzofuranyl 5-thio-β-D-xylopyranoside

By carrying out the process in a manner similar to example 2, starting from the product obtained in example 19, the desired product is obtained in the form of a white solid with a yield of 40%.

Mp=163° C.
$[\alpha]_D^{30} = -52°$ (c=0.33; DMSO).

EXAMPLE 21

2,3-dimethylimidazo[1,2-α]pyridin-8-yl 2,3,4-tri-O-acetyl-5-thio-β-D-xylopyranoside By carrying out the process in a manner similar to process B of example 1, starting from 8-hydroxy-2,3-dimethylimidazo[1,2-α]pyridine, the desired product is obtained in the form of a white solid with a yield of 11%. Mp=213° C.
$[\alpha]_D^{28} = -103°$ (c=0.23; DMSO).

EXAMPLE 22

2,3-dimethylimidazo[1,2-α]pyridin-8-yl 5-thio-β-D-xylopyranoside

By carrying out the process in a manner similar to example 2, starting from the product obtained in example 21, the desired product is obtained in the form of a white solid with a yield of 26%.

Mp=125-130° C.
$[\alpha]_D^{28} = -99°$ (c=0.22; DMSO).

EXAMPLE 23

Imidazo[1,2-α]pyridin-8-yl 2,3,4-tri-O-acetyl-5-thio-β-D-xylopyranoside

By carrying out the process in a manner similar to process A of example 1, starting from bromoacetaldehyde, the desired product is obtained in the form of an ecru solid with a yield of 35%.

Mp=130° C.
$[\alpha]_D^{28} = -76°$ (c=0.50; DMSO).

EXAMPLE 24

Imidazo[1,2-α]pyridin-8-yl 5-thio-β-D-xylopyranoside

By carrying out the process in a manner similar to example 2, starting from the product obtained in example 23, the desired product is obtained in the form of a white solid with a yield of 53%.

Mp=102° C.
$[\alpha]_D^{29} = -52°$ (c=0.20; DMSO).

EXAMPLE 25

2-(1-methylethyl)imidazo[1,2-α]pyridin-8-yl 2,3,4-tri-O-acetyl-5-thio-β-D-xylopyranoside By carrying out the process in a manner similar to process A of example 1, starting from 2-methyl-4-bromo-3-butanone, the desired product is obtained in the form of a white solid with a yield of 31%.

Mp=182° C.
$[\alpha]_D^{35}$=−72° (c=0.20; DMSO).

EXAMPLE 26

2-(1-methylethyl)imidazo[1,2-α]pyridin-8-yl 5-thio-β-D-xylopyranoside

By carrying out the process in a manner similar to example 2, starting from the product obtained in example 25, the desired product is obtained in the form of a white solid with a yield of 55%.

Mp=83° C.
$[\alpha]_D^{35}$=−125° (c=0.20; DMSO).

EXAMPLE 27

2-methylimidazo[1,2-α]pyridin-7-yl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 2-methyl-7-hydroxyimidazo[1,2-α]-pyridine obtained according to preparation 3, the desired product is obtained in the form of a white solid with a yield of 38%. The product obtained is used directly in the deacetylation step.

EXAMPLE 28

2-methylimidazo[1,2-α]pyridin-7-yl 5-thio-β-D-xylopyranoside

By carrying out the process in a manner similar to example 2, starting from the product obtained in example 27, the desired product is obtained in the form of a pinkish solid with a yield of 35%.

Mp=172° C.
$[\alpha]_D^{35}$=−107° (c=0.20; DMSO).

EXAMPLE 29

1-methyl-1H-benzimidazol-4-yl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 4-hydroxy-1-methyl-1H-benzimidazole, the desired product is obtained in the form of a white solid with a yield of 38%. The product obtained is used directly in the deacetylation step.

EXAMPLE 30

1-methyl-1H-benzimidazol-4-yl 5-thio-β-D-xylopyranoside

By carrying out the process in a manner similar to example 8, starting from the product obtained in example 29, the desired product is obtained in the form of a brown solid with a yield of 70%.

Mp=180° C.
$[\alpha]_D^{32}$=−87° (c=0.20; DMSO).

EXAMPLE 31

2-(chloromethyl)imidazo[1,2-α]pyridin-8-yl 2,3,4-tri-O-acetyl-5-thio-β-D-xylopyranoside By carrying out the process in a manner similar to process A of example 1, starting from 1,3-dichloroacetone, the desired product is obtained in the form of a white solid with a yield of 42%.

Mp=166° C.
$[\alpha]_D^{29}$=−75° (c=0.20; DMSO).

EXAMPLE 32

2-(phenylmethyl)imidazo[1,2-α]pyridin-8-yl 2,3,4-tri-O-acetyl-5-thio-β-D-xylopyranoside A solution of 0.108 g (1.02 mM) of sodium carbonate in 2 ml of water, 0.055 g (0.0678 mM) of [1,1'-bis(diphenylphosphino)ferrocene]dichloropalladium (II) dichloromethane and 0.277 g (1.35 mM) of 4,4,5,5-tetramethyl-2-phenyl-1,2,3-dioxaborolane are added to a solution of 0.31 g (0.678 mM) of 2-chloromethylimidazo[1,2-α]pyridin-8-yl 2,3,4-tri-O-acetyl-5-thio-D-xylopyranoside obtained according to example 31, in 4 ml of DME. The reaction mixture is microwave-heated at 120° C. for 30 minutes. After cooling, water is added and the resulting mixture is extracted with ethyl acetate. The organic phase is dried over sodium sulfate and is concentrated under reduced pressure. The evaporation residue is purified by silica gel chromatography, elution being carried out with a dichloromethane/methanol mixture (97/3; v/v), and then crystallized from ether. The expected product is obtained in the form of a white solid with a yield of 42%.

Mp=152° C.
$[\alpha]_D^{29}$=−83° (c=0.19; DMSO).

EXAMPLE 33

2-(phenylmethyl)imidazo[1,2-α]pyridin-8-yl 5-thio-β-D-xylopyranoside

By carrying out the process in a manner similar to example 2, starting from the product obtained in example 32, the desired product is obtained in the form of a white solid with a yield of 90%.

Mp=114° C.
$[\alpha]_D^{29}$=−81° (c=0.20; DMSO).

EXAMPLE 34

2-methylimidazo[1,2-α]pyridin-6-yl 2,3,4-tri-O-acetyl-5-thio-β-D-xylopyranoside

By carrying out the process in a manner similar to example 7, starting from 2,3,4-tri-O-acetyl-5-thio-D-xylopyranosyl bromide and 2-methyl-6-hydroxyimidazo[1,2-α]pyridine obtained according to preparation 5, the desired product is obtained in the form of a white solid with a yield of 13%.

Mp=83° C.
$[\alpha]_D^{24}$=+35° (c=0.20; DMSO).

EXAMPLE 35

2-methylimidazo[1,2-α]pyridin-6-yl 5-thio-β-D-xylopyranoside

By carrying out the process in a manner similar to example 8, starting from the product obtained in example 34, the desired product is obtained in the form of a white solid with a yield of 66%.
Mp=194° C.
$[\alpha]_D^{31}$=−21° (c=1.00; DMSO).

EXAMPLE 36

2-methylimidazo[1,2-α]pyridin-8-yl 2,3-O-(1-methylethylidene)-5-thio-β-D-xylopyranoside A solution of 725 mg (2.66 mM) of 2-methylimidazo[1,2-α]pyridin-8-yl 5-thio-β-D-xylopyranoside (example 2) and 406 mg (5.63 mM) of 2-methoxypropene in 1.5 ml of DMF is prepared at ambient temperature and is then cooled to −8° C. 710 mg (3.05 mM) of camphorsulfonic acid are added to this solution and the resulting mixture is kept stirring at ambient temperature for 24 h. The reaction medium is poured into a solution of sodium bicarbonate (0.5 N) and extracted with ethyl acetate. The organic phase is washed with a saturated solution of sodium chloride and then dried over magnesium sulfate and concentrated under vacuum. The residue obtained is purified by silica gel chromatography, elution being carried out with a dichloromethane/methanol mixture (88/12; v/v). The expected product is obtained in the form of a white powder with a yield of 7%.
Mp=196° C.
$[\alpha]_D^{30}$=−252° (c=0.25; CHCl$_3$).

EXAMPLE 37

2-methylimidazo[1,2-α]pyridin-8-yl 3,4-O-(1-methylethylidene)-5-thio-β-D-xylopyranoside This compound is obtained at the same time as the compound of example 36. The two products are separated during the purification on silica gel. The expected product is obtained in the form of a white powder with a yield of 16.5%.
Mp=190° C.
$[\alpha]_D^{30}$=−252° (c=0.2; CHCl$_3$).

EXAMPLE 38

[1,2,4]triazolo[1,5-a]pyridin-8-yl 2,3,4-tri-O-acetyl-5-thio-β-D-xylopyranoside 0.1 ml of pyridine and 0.068 g (0.6 mM) of hydroxylamine-O-sulfonic acid are added to a solution of 0.22 g (0.5 mM) of the compound obtained according to preparation 6, in 5 ml of methanol. The mixture is stirred at ambient temperature for 2 h, and a white precipitate is obtained. The reaction mixture is subsequently concentrated under reduced pressure. The evaporation residue is solubilized in dichloromethane and the organic phase is washed with water. The organic phase is subsequently dried over sodium sulfate and concentrated under reduced pressure. The residue obtained is purified by silica gel chromatography, elution being carried out with a dichloromethane/ethyl acetate mixture (gradient of 90/10 to 80/20; v/v). The desired product (as a mixture with the starting product of the preceding step) is obtained in the form of a white solid with a yield of 30%. The product is subsequently used in the following step without further purification.

EXAMPLE 39

[1,2,4]triazolo[1,5-a]pyridin-8-yl 5-thio-β-D-xylopyranoside

A mixture consisting of the product obtained in example 38, in 5 ml of a 7 M solution of ammonia in methanol, is stirred at ambient temperature for 3 hours. The reaction mixture is concentrated under reduced pressure and the crude product obtained is purified by silica gel chromatography, elution being carried out with a dichloromethane/methanol mixture (97/3; v/v). The product obtained is washed with cold water and then filtered and dried. The desired product is obtained in the form of a white solid with a yield of 36%.
Mp=155° C.
$[\alpha]_D^{32}$−106° (c=0.2; DMSO).

EXAMPLE 40

2,1-benzisoxazol-7-yl 2,3,4-tri-O-acetyl-5-thio-β-D-xylopyranoside

A mixture composed of 0.25 g (1.85 mM) of anhydrous zinc chloride, and 0.22 g of molecular sieve 13×, in 2 ml of toluene and 2 ml of acetonitrile is stirred, and 0.1 g (0.74 mM) of 2,1-benzisoxazol-7-ol obtained according to preparation 7 and 0.19 g (1.85 mM) of triethylamine are added. The mixture is brought to 90° C. and, while maintaining this temperature, 0.29 g (0.82 mM) of 2,3,4-tri-O-acetyl-5-thio-D-xylopyranosyl bromide is added. The mixture maintained at 90° C. is stirred for a further 20 minutes. The mixture is subsequently cooled, filtered and then concentrated under reduced pressure. The evaporation residue is purified by silica gel chromatography, elution being carried out with a methylcyclohexane/ethyl acetate mixture (gradient 100/0 to 50/50; v/v). The desired product is obtained in the form of a beige solid with a yield of 30%.
Mp=157° C.
$[\alpha]_D^{25}$=−38° (c=0.14; DMSO).

EXAMPLE 41

2,1-benzisoxazol-7-yl 5-thio-β-D-xylopyranoside

A mixture consisting of the product obtained according to example 40, in 5 ml of methanol, and 10 drops of solution of sodium methoxide at 8% in methanol is stirred at ambient temperature for 3 hours. The reaction medium is subsequently neutralized using IR 120H$^+$ resin to pH=5, filtered and concentrated under reduced pressure. The crude product obtained is purified by silica gel chromatography, elution being carried out with a dichloromethane/methanol mixture (gradient of 100/0 to 80/20; v/v), and then by semi-preparative HPLC (column: Waters, Atlantis, 19×100 mm. Eluant: gradient of acetonitrile/H$_2$O/0.1% TFA). The desired product is obtained in the form of a beige solid with a yield of 32%.
Mp=115° C.
$[\alpha]_D^{28}$=−116° (c=0.11; DMSO).

EXAMPLE 42

8-[(2,3,4-tri-O-acetyl-5-thio-β-D-xylopyranosyl)oxy]-imidazo[1,2-α]-pyridine-2-acetic Acid Ethyl Ester By carrying out the process in a manner similar to process A of example 1, starting from 2-amino-3-pyridinyl 2,3,4-tri-O-acetyl-5-thio-β-D-xylopyranoside and 4-chloro-3-oxobutanoic acid ethyl ester, the desired product is obtained in the form of a white solid with a yield of 54%.

Mp=120° C.
$[\alpha]_D^{30}=-75°$ (c=0.29; DMSO).

EXAMPLE 43

8-[(5-thio-β-D-xylopyranosyl)oxy]-imidazo[1,2-α]pyridine-2-acetic acid, salt with trifluoroacetic acid 6 ml of water and then 0.23 g (5.55 mM) of lithium hydroxide are added to a solution of 0.55 g (1.11 mM) of the compound obtained according to example 42, in 6 ml of THF, and the mixture is stirred at ambient temperature overnight. The reaction mixture is concentrated under reduced pressure and then acidified with a solution of hydrochloric acid (1 M) to pH=3-4, and lyophilized. The product obtained is, finally, purified by semi-preparative HPLC (column: Waters, Atlantis, 19×100 mm. Eluant: gradient of acetonitrile/H$_2$O/0.1% TFA). The desired product is obtained in the form of its salt with trifluoroacetic acid, in the form of a white cotton-like substance with a yield of 31%.

Mp=86° C.
$[\alpha]_D^{27}=-54'$ (c=0.33; DMSO).

EXAMPLE 44

2-methyl-6-benzothiazolyl 2,3,4-tri-O-acetyl-5-thio-β-D-xylopyranoside

By carrying out the process in a manner similar to example 7, starting from 2-methyl-6-hydroxybenzothiazole, the desired product is obtained in the form of an ecru solid with a yield of 24%.

Mp=160° C.
$[\alpha]_D^{28}=-3°$ (c=0.3; DMSO).

EXAMPLE 45

2-methyl-6-benzothiazolyl 5-thio-β-D-xylopyranoside

By carrying out the process in a manner similar to example 2, starting from the product obtained according to example 44, the desired product is obtained in the form of a white solid with a yield of 70%.

Mp=184° C.
$[\alpha]^{27}=-40°$ (c=0.34; DMSO).

EXAMPLE 46

2-methyl-5-benzoxazolyl 2,3,4-tri-O-acetyl-5-thio-β-D-xylopyranoside

By carrying out the process in a manner similar to example 7, starting from 2-methyl-5-hydroxybenzoxazole, the desired product is obtained in the form of a white solid with a yield of 26%.

Mp=168° C.
$[\alpha]_D^{28}=-30°$ (c=0.12; DMSO).

EXAMPLE 47

2-methyl-5-benzoxazolyl 5-thio-β-D-xylopyranoside

By carrying out the process in a manner similar to example 2, starting from the product obtained according to example 46, the desired product is obtained, after crystallization from 2-propanol, in the form of a white solid with a yield of 62%.

Mp=187-189° C.
$[\alpha]_D^{25}=-86°$ (c=0.23; DMSO).

EXAMPLE 48

2-methyl-4-benzoxazolyl 2,3,4-tri-O-acetyl-5-thio-β-D-xylopyranoside

By carrying out the process in a manner similar to example 7, starting from 2-methyl-4-hydroxybenzoxazole, the desired product is obtained in the form of a white solid with a yield of 9%.

Mp=149-151° C.
$[\alpha]_D^{25}=-55°$ (c=0.27; DMSO).

EXAMPLE 49

2-methyl-4-benzoxazolyl 5-thio-β-D-xylopyranoside

By carrying out the process in a manner similar to example 2, starting from the product obtained according to example 48, the desired product is obtained, after crystallization from water, in the form of a white solid with a yield of 91%.

Mp=164-167° C.
$[\alpha]_D^{25}=-73°$ (c=0.53; DMSO).

EXAMPLE 50

3-methyl-1,2-benzisoxazol-4-yl 2,3,4-tri-O-acetyl-5-thio-β-D-xylopyranoside

By carrying out the process in a manner similar to example 7, starting from 3-methyl-4-hydroxy-1,2-benzisoxazole, the desired product is obtained in the form of a cream solid with a yield of 14%.

Mp=155-158° C. (MeOH).
$[\alpha]_D^{25}=-83°$ (c=0.78; DMSO).

EXAMPLE 51

3-methyl-1,2-benzisoxazol-4-yl 5-thio-β-D-xylopyranoside

By carrying out the process in a manner similar to example 2, starting from the compound obtained according to example 50, the expected product is obtained, after crystallization from water, in the form of a white solid with a yield of 89%.

Mp=165-168° C.
$[\alpha]_D^{28}=-74°$ (c=0.18; DMSO).

EXAMPLE 52

1-methyl-1H-1,2,3-benzotriazol-5-yl 2,3,4-tri-O-acetyl-5-thio-β-D-xylopyranoside By carrying out the process in a manner similar to example 7, starting from 5-hydroxy-1-methyl-1H-1,2,3-benzotriazole, the desired product is obtained in the form of a white solid with a yield of 11%.

Mp=80° C.
$[\alpha]_D^{28}=-9°$ (c=0.26; DMSO).

EXAMPLE 53

1-methyl-1H-1,2,3-benzotriazol-5-yl 5-thio-β-D-xylopyranoside

By carrying out the process in a manner similar to example 2, starting from the compound obtained according to example 52, the desired product is obtained in the form of a white solid with a yield of 61%.

Mp=220° C.
$[\alpha]_D^{25}$=−113° (c=0.26; DMSO).

EXAMPLE 54

6-benzothiazolyl 2,3,4-tri-O-acetyl-5-thio-β-D-xylo-pyranoside

By carrying out the process in a manner similar to example 7, starting from 6-hydroxybenzothiazole, the expected product is obtained in the form of a white solid with a yield of 30%.

Mp=166° C.
$[\alpha]_D^{27}$=−2.4° (c=0.2; DMSO).

EXAMPLE 55

6-benzothiazolyl-5-thio-β-D-xylopyranoside

By carrying out the process in a manner similar to example 2, starting from the compound obtained according to example 54, the desired product is obtained in the form of a white solid with a yield of 72%.

Mp=192° C.
$[\alpha]_D^{27}$=−48° (c=0.25; DMSO).

EXAMPLE 56

6-[(2,3,4-tri-O-acetyl-5-thio-β-D-xylopyranosyl)oxy]-1H-indole-1-carboxylic Acid, 1,1-dimethylethyl Ester A solution of 2.66 g (11.41 mM) of 6-hydroxy-1H-indole-1-carboxylic acid tert-butyl ester in 50 ml of THF, 4.16 g (20.6 mM) of diisopropylazodicarboxylate and 5.39 g (20.6 mM) of triphenylphosphine are added to a solution of 4.34 g (14.84 mM) of 2,3,4-tri-O-acetyl-5-thio-D-xylopyranose in 150 ml of THF. The reaction mixture is stirred at 50° C. for 4 hours and then concentrated under reduced pressure. The evaporation residue is solubilized in ethyl acetate and the organic phase is washed with a 1N solution of sodium hydroxide and then with a concentrated aqueous solution of ammonium chloride. The organic phase is subsequently dried over magnesium sulfate and concentrated under reduced pressure. The evaporation residue is purified by silica gel chromatography, elution being carried out with a methylcyclohexane/ethyl acetate mixture (gradient of 9/1 to 7/3; v/v). The residue obtained is subsequently purified by $C_{18}$-grafted silica chromatography, elution being carried out with an acetonitrile/water mixture (6/4; v/v). The desired product is obtained in the form of a white solid with a yield of 3%.

Mp=147-158° C.
$[\alpha]_D^{28}$=14° (c=0.11; DMSO).

EXAMPLE 57

1H-indol-6-yl 2,3,4-tri-O-acetyl-5-thio-β-D-xylopyranoside 0.092 g (0.085 mM) of anisole and 0.5 ml of trifluoroacetic acid are added to a solution of 0.043 g (0.085 mM) of the compound obtained according to example 56, in 4.5 ml of dichloromethane. The reaction mixture is stirred at reflux for 3 h and then, after cooling, concentrated under reduced pressure. The evaporation residue is purified by semi-preparative HPLC (column: Waters, Atlantis, 19×100 mm. Eluant: gradient of acetonitrile/$H_2O$/0.1% TFA). The desired product is obtained in the form of a greyish-white solid with a yield of 16%.

Mp=172-175° C.
$[\alpha]_D^{23}$=−10° (c=0.16 DMSO).

EXAMPLE 58

3-methyl-1,2-benzisoxazol-6-yl 2,3,4-tri-O-acetyl-5-thio-β-D-xylopyranoside

By carrying out the process in a manner similar to example 7, starting from the product obtained according to preparation 8, the desired product is obtained in the form of a white solid with a yield of 17%.

Mp=170-180° C.
$[\alpha]_D^{22}$=−7° (c=0.33 DMSO).

EXAMPLE 59

3-methyl-1,2-benzisoxazol-6-yl 5-thio-β-D-xylopyranoside

By carrying out the process in a manner similar to example 41, starting from the compound obtained according to example 58, the desired product is obtained in the form of a white solid with a yield of 53%.

Mp=148-161° C.
$[\alpha]_D^{23}$=−79° (c=0.13 DMSO).

EXAMPLE 60

1-methyl-1H-1,2,3-benzotriazol-6-yl 2,3,4-tri-O-acetyl-5-thio-β-D-xylopyranoside By carrying out the process in a manner similar to example 7, starting from 1-methyl-1H-1,2,3-benzotriazol-6-ol, the desired product is obtained in the form of a white solid with a yield of 60%.

Mp=143° C.
$[\alpha]_D^{24}$=3° (c=0.2 DMSO).

EXAMPLE 61

1-methyl-1H-1,2,3-benzotriazol-6-yl 5-thio-β-D-xylopyranoside

By carrying out the process in a manner similar to example 2, starting from the product obtained according to example 60, the desired product is obtained, after crystallization from water, in the form of a white solid with a yield of 51%.

Mp=211° C.
$[\alpha]_D^{25}$=−86° (c=0.24; DMSO).

EXAMPLE 62

1,2-dimethyl-1H-benzimidazol-4-yl 2,3,4-tri-O-acetyl-5-thio-β-D-xylopyranoside

By carrying out the process in a manner similar to example 7, starting from 1,2-dimethyl-4-hydroxy-1H-benzimidazole, the desired product is obtained in the form of a beige powder with a yield of 4%.

Mp=192° C.
$[\alpha]_D^{24} = -11°$ (c=0.11 DMSO).

EXAMPLE 63

1,2-dimethyl-1H-benzimidazol-4-yl 5-thio-β-D-xylopyranoside

By carrying out the process in a manner similar to example 2, starting from the product obtained according to example 62, the desired product is obtained in the form of a brown powder with a yield of 20%.

Mp 153° C.
$[\alpha]_D^{26} = -37°$ (c=0.2; DMSO).

The structures of the compounds of formula I described above are reiterated in the table below:

(I)

| Ex | X1 | X2 | Y1 | Y2 | R1 | R2 | R3 | R4 | R5 | R' | R'' | R''' | TX |
|---|---|---|---|---|---|---|---|---|---|---|---|---|---|
| 1 | N | C | C | N | H | H | H | 2-CH$_3$ | H | Ac | Ac | Ac | 8 |
| 2 | N | C | C | N | H | H | H | 2-CH$_3$ | H | H | H | H | 8 |
| 3 | N | C | C | N | H | H | H | 2-C$_6$H$_5$ | H | Ac | Ac | Ac | 8 |
| 4 | N | C | C | N | H | H | H | 2-C$_6$H$_5$ | H | H | H | H | 8 |
| 5 | N | C | C | N | H | H | H | 3-CH$_3$ | H | Ac | Ac | Ac | 8 |
| 6 | N | C | C | N | H | H | H | 3-CH$_3$ | H | H | H | H | 8 |
| 7 | C | C | C | O | H | H | H | 2-Ac | H | Ac | Ac | Ac | 7 |
| 8 | C | C | C | O | H | H | H | 2-Ac | H | H | H | H | 7 |
| 9 | C | C | C | N | H | H | H | H | 2 and 3-H | Ac | Ac | Ac | 5 |
| 10 | C | C | C | N | H | H | H | H | 2 and 3-H | H | H | H | 5 |
| 11 | C | S | C | N | H | H | H | 2-CH$_3$ | — | Ac | Ac | Ac | 5 |
| 12 | C | S | C | N | H | H | H | 2-CH$_3$ | — | H | H | H | 5 |
| 13 | C | C | C | O | 4-OCH$_3$ | 7-OCH$_3$ | 5-Ac | H | H | Ac | Ac | Ac | 6 |
| 14 | C | C | C | O | 4-OCH$_3$ | 7-OCH$_3$ | 5-Ac | H | H | H | H | H | 6 |
| 15 | C | N | C | O | H | H | H | H | — | Ac | Ac | Ac | 4 |
| 16 | C | N | C | O | H | H | H | H | — | H | H | H | 4 |
| 17 | C | C | C | O | H | H | H | H | H | Ac | Ac | Ac | 7 |
| 18 | C | C | C | O | H | H | H | H | H | H | H | H | 7 |
| 19 | C | C | C | O | H | H | H | 3-Bz | H | Ac | Ac | Ac | 5 |
| 20 | C | C | C | O | H | H | H | 3-Bz | H | H | H | H | 5 |
| 21 | N | C | C | N | H | H | H | 2-CH$_3$ | 3-CH$_3$ | Ac | Ac | Ac | 8 |
| 22 | N | C | C | N | H | H | H | 2-CH$_3$ | 3-CH$_3$ | H | H | H | 8 |
| 23 | N | C | C | N | H | H | H | H | H | Ac | Ac | Ac | 8 |
| 24 | N | C | C | N | H | H | H | H | H | H | H | H | 8 |
| 25 | N | C | C | N | H | H | H | 2-CH(CH$_3$)$_2$ | H | Ac | Ac | Ac | 8 |
| 26 | N | C | C | N | H | H | H | 2-CH(CH$_3$)$_2$ | H | H | H | H | 8 |
| 27 | N | C | C | N | H | H | H | 2-CH$_3$ | H | Ac | Ac | Ac | 7 |
| 28 | N | C | C | N | H | H | H | 2-CH$_3$ | H | H | H | H | 7 |
| 29 | C | N | C | N | H | H | H | 1-CH$_3$ | H | Ac | Ac | Ac | 4 |
| 30 | C | N | C | N | H | H | H | 1-CH$_3$ | H | H | H | H | 4 |
| 31 | N | C | C | N | H | H | H | 2-CH$_2$Cl | H | Ac | Ac | Ac | 8 |
| 32 | N | C | C | N | H | H | H | 2-Bn | H | Ac | Ac | Ac | 8 |
| 33 | N | C | C | N | H | H | H | 2-Bn | H | H | H | H | 8 |
| 34 | N | C | C | N | H | H | H | 2-CH$_3$ | H | Ac | Ac | Ac | 6 |
| 35 | N | C | C | N | H | H | H | 2-CH$_3$ | H | H | H | H | 6 |
| 36* | N | C | C | N | H | H | H | 2-CH$_3$ | H | H | 2,3-ip | | 8 |
| 37* | N | C | C | N | H | H | H | 2-CH$_3$ | H | 3,4-ip | H | | 8 |
| 38 | N | N | C | N | H | H | H | H | — | Ac | Ac | Ac | 8 |
| 39 | N | N | C | N | H | H | H | H | — | H | H | H | 8 |
| 40 | C | N | O | C | H | H | H | H | — | Ac | Ac | Ac | 7 |
| 41 | C | N | O | C | H | H | H | H | — | H | H | H | 7 |
| 42 | N | C | C | N | H | H | H | —CH$_2$—CO$_2$Et | H | Ac | Ac | Ac | 8 |
| 43# | N | C | C | N | H | H | H | —CH$_2$—CO$_2$H | H | H | H | H | 8 |
| 44 | C | N | C | S | H | H | H | 2-CH$_3$ | — | Ac | Ac | Ac | 6 |
| 45 | C | N | C | S | H | H | H | 2-CH$_3$ | — | H | H | H | 6 |
| 46 | C | N | C | O | H | H | H | 2-CH$_3$ | — | Ac | Ac | Ac | 5 |
| 47 | C | N | C | O | H | H | H | 2-CH$_3$ | — | H | H | H | 5 |
| 48 | C | N | C | O | H | H | H | 2-CH$_3$ | — | Ac | Ac | Ac | 4 |

-continued

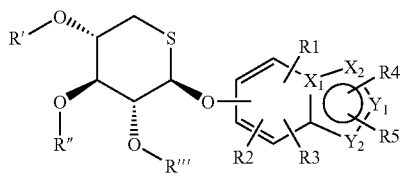

(I)

| Ex | X1 | X2 | Y1 | Y2 | R1 | R2 | R3 | R4 | R5 | R' | R" | R''' | TX |
|---|---|---|---|---|---|---|---|---|---|---|---|---|---|
| 49 | C | N | C | O | H | H | H | 2-CH₃ | — | H | H | H | 4 |
| 50 | C | C | N | O | H | H | H | 3-CH₃ | — | Ac | Ac | Ac | 4 |
| 51 | C | C | N | O | H | H | H | 3-CH₃ | — | H | H | H | 4 |
| 52 | C | N | N | N | H | H | H | 1-CH₃ | — | Ac | Ac | Ac | 5 |
| 53 | C | N | N | N | H | H | H | 1-CH₃ | — | H | H | H | 5 |
| 54 | C | N | C | S | H | H | H | H | — | Ac | Ac | Ac | 6 |
| 55 | C | N | C | S | H | H | H | H | — | H | H | H | 6 |
| 56 | C | C | C | N | H | H | H | 1-CO₂—tBu | 2 and 3-H | Ac | Ac | Ac | 6 |
| 57 | C | C | C | N | H | H | H | H | 2 and 3-H | H | H | H | 6 |
| 58 | C | C | N | O | H | H | H | 3-CH₃ | — | Ac | Ac | Ac | 6 |
| 59 | C | C | N | O | H | H | H | 3-CH₃ | — | H | H | H | 6 |
| 60 | C | N | N | N | H | H | H | 1-CH₃ | — | Ac | Ac | Ac | 6 |
| 61 | C | N | N | N | H | H | H | 1-CH₃ | — | H | H | H | 6 |
| 62 | C | N | C | N | H | H | H | 1-CH₃ | 2-CH₃ | Ac | Ac | Ac | 4 |
| 63 | C | N | C | N | H | H | H | 1-CH₃ | 2-CH₃ | H | H | H | 4 |

TX indicates the thioxylose substitution position
Ac = COCH₃
Bz = benzoyl
Bn = benzyl
*ip signifies an isopropylidene (or 1-methylethylidene) bridge
salt with trifluoroacetic acid The antithrombotic activity of the compounds according to the invention was studied in vivo in rats by virtue of a test that reproduces a venous thrombosis.

The venous thrombosis was induced according to the protocol described in *Thromb. Haemost.* 1992, 67 (1), 176-179. The activity by oral administration was studied according to the following operating protocol:

The experiment is carried out on male Wistar rats, not fasting, weighing 250 to 280 g and divided up into groups, each of 8 to 10 animals. The test products are administered orally (by tube) in solution or in suspension in a solution of methylcellulose (0.5% in water). The concentration of the compounds is calculated such that an amount of solution of 10 ml/kg is absorbed orally. A thrombosis is induced at a time T (between 2 hours and 8 hours) after administration of the product, and the thrombus formed is removed and weighed. In order to induce this thrombosis, a venous stasis with hypercoagulation is produced, according to the technique described by WESSLER (*J. Applied Physiol.* 1959, 943-946) using, as hypercoagulating agent, a solution of activated factor X (Xa), supplied by the company Biogenic (Montpellier), and having a concentration of 7.5 nKat/kg. The venous stasis is produced exactly 10 seconds after the injection of the hypercoagulating agent. The activity of the compounds tested was verified at various doses, after they were administered. The thrombosis was induced between 2 hours and 8 hours after administration of the compound. By way of example, the results of the preceding tests are reported in the table below for some compounds according to the invention (the activity is expressed by the percentage inhibition of the formation of the thrombus, observed in the presence of the compound according to the invention, relative to the weight of the thrombus formed in the absence of the compound).

TABLE I

| | Activity by oral administration | | |
|---|---|---|---|
| Example | Dose (mg/kg) | Time (h) | Activity (%) |
| 2 | 6 | 2 | 94 |
| 8 | 6 | 2 | 91 |
| 12 | 6 | 2 | 74 |
| 16 | 6 | 2 | 80 |
| 18 | 6 | 2 | 62 |
| 39 | 6 | 2 | 100 |
| 43 | 6 | 2 | 53 |

These results show that the compounds according to the invention have an activity against venous thrombosis.

A subject of the present invention is therefore a compound of formula I according to the invention, and also the pharmaceutically acceptable salts thereof with an acid, solvates thereof and hydrates thereof, for their use as a medicament. The compound of formula I or a pharmaceutically acceptable salt, solvate or hydrate thereof may be used for the preparation of an antithrombotic medicament for use, in particular, in the treatment or prevention of venous circulation conditions, and especially for correcting certain hematological parameters that are sensitive at the venous level.

A subject of the present invention is also therefore pharmaceutical compositions containing a compound of formula I or a pharmaceutically acceptable salt, solvate or hydrate thereof. These pharmaceutical compositions in general contain suitable excipients. Said excipients are chosen according to the pharmaceutical form and the route of administration desired, in particular oral administration or administration by injection.

These pharmaceutical compositions are prepared according to the conventional methods known to those skilled in the art. For example, the compounds according to the invention may be formulated with physiologically acceptable excipients in order to obtain an injectable form to be used directly, an injectable form to be prepared extemporaneously or a solid form for oral administration, such as, for example, a gel capsule or a tablet.

By way of example, an injectable form may preferably be prepared by lyophilizing a filtered and sterilized solution containing the compound according to the invention and a soluble excipient in an amount necessary and sufficient to obtain an isotonic solution after extemporaneous addition of water for injection. The solution obtained may be administered either as a single subcutaneous or intramuscular injection, or in the form of a slow perfusion. A form for oral administration will preferably be in the form of a gel capsule containing the compound of the invention, finely ground, or better still micronized, and mixed with excipients known to those skilled in the art, for instance lactose, pregelatinized starch or magnesium stearate.

In order to obtain the desired therapeutic or prophylactic effect, each unit dose may contain 10 to 500 mg of at least one compound according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A thioxylose compound selected from the group consisting of:
   a) compounds of formula I:

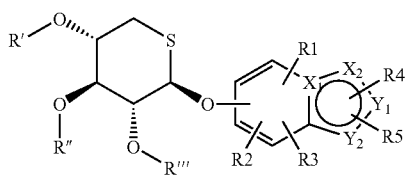

(I)

in which:
the pentapyranosyl group represents a free or substituted 5-thio-β-D-xylopyranosyl group,
R', R" and R'" each independently represent a hydrogen atom or a $C_2$-$C_6$ acyl group, or two of them, adjacent, form a 1-methylethylidene bridge,
$X_1$ and $X_2$ each represent a carbon or nitrogen atom,
$Y_1$ and $Y_2$ each represent, independently of one another, a carbon, nitrogen, sulfur or oxygen atom, with the condition that, if $Y_2$ represents an oxygen or sulfur atom, $Y_1$ represents a carbon or nitrogen atom,
$R_1$, $R_2$, $R_3$, $R_4$ and $R_5$ represent, independently of one another, a hydrogen atom, a —$COOR_6$ group where $R_6$ represents a hydrogen atom or a $C_1$-$C_4$ alkyl, a $C_1$-$C_4$ alkyl group optionally substituted with a phenyl ring, a halogen atom or a —$COOR_6$ group; a $C_1$-$C_4$ alkoxy group, a $C_2$-$C_6$ acyl group, a benzoyl group or a phenyl ring;
   b) addition salts of the compounds of formula I;
   c) active metabolites of the compounds of formula I.

2. A compound as claimed in claim 1, wherein $R_1$, $R_2$, $R_3$, $R_4$ and $R_5$ each independently represent a hydrogen atom, a $C_1$-$C_4$ alkyl group optionally substituted with a phenyl ring or a halogen atom, a $C_1$-$C_4$ alkoxy group, a $C_2$-$C_6$ acyl group, a benzoyl group or a phenyl ring.

3. A compound as claimed in claim 1, wherein $X_1$ and $Y_2$ each represent a nitrogen atom, and $X_2$ and $Y_1$ each represent a carbon atom.

4. A compound as claimed in claim 1, wherein R', R" and R'" each represent a hydrogen atom.

5. A compound as claimed in claim 1, wherein R', R" and R'" each represent a $COCH_3$ group.

6. A process for producing a compound as claimed in claim 1, said process comprising:
   a) reacting an aromatic system comprising a hydroxyl group that is phenolic in nature, corresponding to formula II:

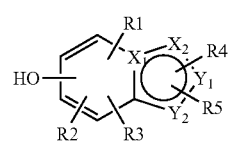

II in which:
$X_1$ and $X_2$ each represent a carbon or nitrogen atom,
$Y_1$ and $Y_2$ represent a carbon, nitrogen, sulfur or oxygen atom, with the proviso that, if $Y_2$ represents an oxygen or sulfur atom, $Y_1$ represents a carbon or nitrogen atom,
$R_1$, $R_2$, $R_3$, $R_4$ and $R_5$ each independently represent a hydrogen atom, a —$COOR_6$ group where $R_6$ represents a hydrogen atom or a $C_1$-$C_4$ alkyl group, a $C_1$-$C_4$ alkyl group optionally substituted with a phenyl ring, a halogen atom or a —$COOR_6$ group; a $C_1$-$C_4$ alkoxy group, a $C_2$-$C_6$ acyl group, a benzoyl group or a phenyl ring, with a 5-thioxylopyranose compound corresponding to formula III-D:

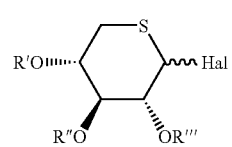

(III-D)

in which Hal represents a halogen, and R', R" and R'" represent a $C_2$-$C_6$ acyl group, in an aprotic solvent, in the presence of a silver salt or silver imidazolate, or of a zinc salt in an anhydrous medium, at a temperature of between 25 and 110° C. for 1 to 10 hours, so as to obtain the compound of formula I:

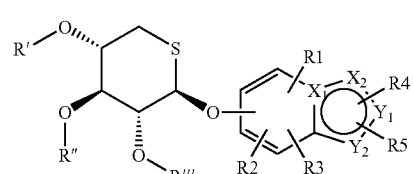

(I)

in which $X_1$, $X_2$, $Y_1$, $Y_2$, R', R", R'", $R_1$, $R_2$, $R_3$, $R_4$ and $R_5$ each have the same meaning as in the starting compounds;

b) optionally reacting the compound of formula I obtained in a) with a solution of ammonia in methanol so as to deacylate the thioxylopyranosyl residue, thereby replacing the acyl groups with hydrogen atoms and obtaining a compound of formula Ia:

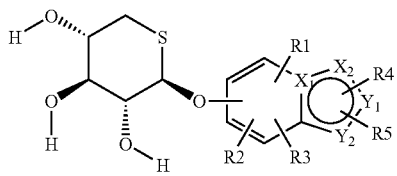

Ia in which $X_1$, $X_2$, $Y_1$, $Y_2$, $R_1$, $R_2$, $R_3$, $R_4$ and $R_5$ have the respective meanings given above;

c) optionally reacting one of the compounds I or Ia obtained above with an acid so as to obtain the corresponding addition salt; and d) optionally reacting the compound of formula Ia obtained above with 2-methoxypropene, in an anhydrous solvent and in an acidic medium, so as to obtain a compound of formula I in which two adjacent substituents selected from the group consisting of R', R" and R''' represent a 1-methylethylidene bridge and the remaining one of R', R" and R''' represents a hydrogen atom.

7. A process as claimed in claim 6, wherein Hal represents bromine; R', R" and R''' each represent an acetyl group; the aprotic solvent is acetonitrile or toluene; the silver salt is silver oxide; or the zinc salt is zinc oxide or zinc chloride.

8. A pharmaceutical composition comprising a compound as claimed in claim 1, and at least one pharmaceutically acceptable carrier or auxiliary substance.

9. A method of treating or inhibiting thromboses in a subject, said method comprising administering to said subject a pharmacologically effective amount of a compound as claimed in claim 1.

10. A method as claimed in claim 9, wherein said thromboses are venous thromboses.

* * * * *